US005693580A

United States Patent [19]
Brow et al.

[11] Patent Number: 5,693,580
[45] Date of Patent: Dec. 2, 1997

[54] TITANIUM SEALING GLASSES AND SEALS FORMED THEREFROM

[75] Inventors: Richard K. Brow; Howard L. McCollister; Carol C. Phifer, all of Albuquerque, N. Mex.; Delbert E. Day, Rolla, Mo.

[73] Assignee: Sandia Corporation, Albuquerque, N. Mex.

[21] Appl. No.: 713,385

[22] Filed: Sep. 13, 1996

[51] Int. Cl.$^6$ ................................. C03C 8/00; C03C 3/15
[52] U.S. Cl. ................. 501/14; 501/50; 501/51; 428/432; 428/433
[58] Field of Search ................. 501/14, 50, 51; 428/432, 433; 174/50.61

[56] References Cited

U.S. PATENT DOCUMENTS

| | | | |
|---|---|---|---|
| 3,081,178 | 3/1963 | Weissenberg et al. | 501/78 |
| 4,945,071 | 7/1990 | Friesen | 501/41 |
| 5,104,738 | 4/1992 | Brow | 428/433 |
| 5,104,755 | 4/1992 | Taylor | 429/181 |
| 5,137,849 | 8/1992 | Brix | 501/15 |
| 5,176,747 | 1/1993 | Panzera et al. | 501/14 |

OTHER PUBLICATIONS

H. Rawson and E.P. Denton, "The Glass Sealing Properties of Titanium and Zirconium," *British Journal of Applied Physics*, vol. 5, pp. 352–353, Oct. 1954.

D. R. Salmi and B. C. Bunker, *Glass Corrosion in Liquid Lithium*, Sandia National Laboratories Report No. SAND83-2314, Sep. 1984.

R. K. Brow and R. D. Watkins, "Reactions and Bonding Between Glasses and Titanium," in *Technology of Glass, Ceramic, or Glass–Ceramic to Metal Sealing*, W. E. Moddeman, C. W. Merten, and D. P. Kramer, editors (The American Society of Mechanical Engineers, New York) pp. 25–30, 1987.

*Primary Examiner*—Karl Group
*Attorney, Agent, or Firm*—John P. Hohimer

[57] ABSTRACT

Alkaline-earth lanthanoborate sealing-glass compositions containing $CaO$, $La_2O_3$, $B_2O_3$, $TiO_2$ and $Al_2O_3$ in various combinations of mole-% are provided. These sealing-glass compositions are useful for forming hermetic glass-to-metal seals with titanium and titanium alloys that have a high aqueous durability for component or device applications requiring exposure to moisture, water or body fluids. Particular applications of the titanium sealing-glass compositions include forming glass-to-metal seals for lithium batteries and implanted biomedical devices (e.g. batteries, pacemakers, defibrillators, pumps).

17 Claims, 2 Drawing Sheets

TITANIUM SEALING GLASSES AND SEALS FORMED THEREFROM

This invention was made with Government support under Contract No. DE-AC04-94AL85000 awarded by the U.S. Department of Energy. The Government has certain rights in the invention.

FIELD OF THE INVENTION

The present invention relates to sealing-glass compositions for forming glass-to-metal seals and, in particular, to sealing-glass compositions having an improved aqueous durability for forming hermetic glass-to-metal seals with titanium and titanium alloys for use with components or devices exposed to water or body fluids (e.g. implantable devices).

BACKGROUND OF THE INVENTION

Titanium and titanium alloys have a number of outstanding properties, including high strength-to-weight ratios and excellent resistances to chemical attack, that make them desirable materials for many component applications. The usefulness of titanium and titanium alloys for component or device design has been limited by the lack of a hermetic sealing technology for forming glass-to-metal seals having a high aqueous durability (e.g. sufficiently high for use in vivo, or for applications requiring prolonged exposure to moisture or water). Interfacial reactions between titanium and commercial silicate sealing glasses promote alkali volatilization and the formation of a weakly adherent silicide phase that generally results in poor seal integrity.

Boroaluminate glasses as disclosed in U.S. Pat. No. 5,104,738 to Brow et al are potential candidates for titanium glass-to-metal seals since they have a coefficient of thermal expansion close to that of titanium and a mechanical strength exceeding that of the commercial silicate sealing glasses. However, the boroaluminate glasses have sufficiently poor aqueous durabilities to be excluded from use in components that are in prolonged contact with water, moisture or body fluids (e.g. in vivo components or devices such as batteries, heart pacemakers, defibrillators, pumps or the like).

Thus, there is a need for improved titanium sealing-glass compositions having a high aqueous durability suitable for forming glass-to-metal seals with titanium and titanium alloys for prolonged exposure to moisture or water, and for in vivo use. For in vivo use, the titanium sealing-glass compositions should also be free of any constituents that are known to be toxic to humans.

An advantage of the titanium sealing-glass compositions according to the present invention is that glass-to-metal seals can be formed with titanium or titanium alloys having an aqueous durability that exceeds the aqueous durability of boroaluminate glasses by up to a thousand-fold or more.

Another advantage of the present invention is that the titanium sealing-glass compositions according to the present invention can be used for forming titanium glass-to-metal seals for in vivo applications including implantable batteries, pacemakers, defibrillators and pumps.

A further advantage is that the titanium sealing-glass compositions of the present invention can be used for forming a compound glass-to-metal seal for lithium batteries, with the compound glass-to-metal seal comprising an outer seal for providing a substantial chemical resistance to water, moisture or body fluids, and an inner seal for providing a substantial chemical resistance to lithium (e.g. a lithium electrode).

These and other advantages of the titanium sealing glasses of the present invention will become evident to those skilled in the art.

SUMMARY OF THE INVENTION

A sealing-glass composition is provided with an improved aqueous durability for forming a glass-to-metal seal with titanium or a titanium alloy. The titanium sealing-glass composition comprises calcium oxide (CaO) in the amount of 10–43 mole-%; lanthanum oxide ($La_2O_3$) in the amount of 8–30 mole-%; and boron oxide ($B_2O_3$) in the amount of 31–57 mole-%. The sealing-glass composition can further include titanium dioxide ($TiO_2$) in the amount of 0–41 mole-% and/or aluminum oxide ($Al_2O_3$) in the amount of 0–28 mole-%. Examples of the titanium sealing-glass compositions of the present invention containing lanthanum have a coefficient of thermal expansion near that of titanium or titanium alloys, and also preferably have a sealing temperature less than about 900° C. The titanium sealing-glass composition is further silicate-free (i.e. no included $SiO_2$), and useful for forming hermetic glass-to-metal seals with a high aqueous durability (e.g. for providing a feedthrough for one or more electrical connections of a device that is exposed to moisture, water or body fluids).

Other advantages and novel features of the invention will become apparent from the following detailed description thereof when considered in conjunction with the accompanying drawings.

BRIEF DESCRIPTION OF THE DRAWINGS

The accompanying drawings, which are incorporated into and form a part of the specification, illustrate several aspects of the present invention and, together with the description, serve to explain the principles of the invention. The drawings are only for the purpose of illustrating preferred embodiments of the invention and are not to be construed as limiting the invention. In the drawings.

DETAILED DESCRIPTION OF THE INVENTION

Figure 1:
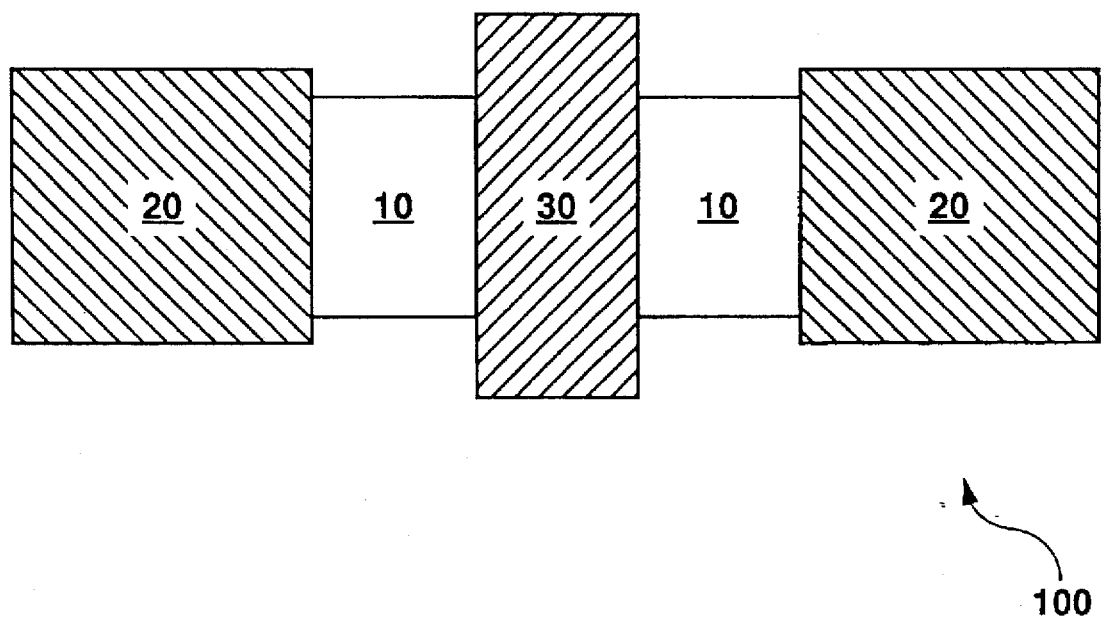
FIG. 1 shows a schematic cross-section diagram of a first example of a glass-to-metal seal formed with a titanium sealing-glass composition according to the present invention.

The titanium sealing glasses of the present invention comprise alkaline-earth lanthanoborate compositions with or without added titanium dioxide ($TiO_2$) and aluminum oxide ($Al_2O_3$). Compositional ranges for constituent oxides of the alkaline-earth lanthanoborate sealing glasses of the present invention are listed below in Table 1:

TABLE 1

Compositional Ranges for Alkaline-Earth Lanthanoborate Sealing Glasses

| Oxide | Compositional Range (mole-%) |
|---|---|
| CaO | 10–43 |
| $La_2O_3$ | 8–30 |
| $B_2O_3$ | 31–57 |
| $TiO_2$ | 0–41 |
| $Al_2O_3$ | 0–28 |

The above oxides upon fusing produce glass compositions having thermal expansion and favorable viscosity characteristics that are substantially matched to titanium and titanium alloys for forming glass-to-metal seals thereto that are near-stress-free or in compression. Silica (i.e. $SiO_2$) is not used in forming the above alkaline-earth lanthanoborate sealing-glass compositions to prevent formation of titanium silicide which can limit adherence of the sealing-glass to titanium.

The alkaline-earth lanthanoborate sealing-glass compositions (also referred to herein as titanium sealing-glass compositions including lanthanum) of the present invention can be prepared from predetermined amounts of reagent grade raw materials in the above compositional ranges, including oxides of calcium (CaO), lanthanum ($La_2O_3$) and boric acid ($H_3BO_3$); with or without added oxides of titanium ($TiO_2$) and aluminum ($Al_2O_3$). Particular lanthanum-containing titanium sealing-glass compositions can be formed, for example, by melting oxide raw materials in the above compositional ranges in a platinum crucible in air at about 1400° C. for about five hours with periodic stirring (at least twice) of the melt. As formed, the sealing-glass compositions are homogeneous and substantially clear.

From the glass melt, sealing-glass preforms of a predetermined size can be formed by casting into preheated molds. The sealing-glass preforms are then preferably annealed for about 15–20 minutes at or near the glass transition temperature, $T_g$, which can be determined by differential thermal analysis (DTA). Glass-to-metal seals can then be formed from the sealing-glass compositions of the present invention (i.e. from the sealing-glass preforms) in contact with titanium or a titanium alloy using conventional seal-forming techniques in either a continuous belt or batch furnace. Particular sealing-glass compositions according to the present invention can have a coefficient of thermal expansion (CTE) that is within about 5% of that of titanium or a titanium alloy (the CTE of Ti and Ti-alloys is about 90–100×10$^{-7}$° C.$^{-1}$) as measured, for example, by dilatometry (e.g. with a dual pushrod dilatometer from room temperature up to about 500° C.).

Examples of particular silicate-free titanium sealing-glass compositions including lanthanum according to the present invention are provided in Table 2, together with measured

TABLE 2

Analyzed Composition (mole-%) and Thermal Properties of Examples of Silicate-Free Titanium Sealing-Glasses Including Lanthanum

| Glass Composition | TIG-9 | TIG-17 | TIG-23 | TIG-24 |
|---|---|---|---|---|
| CaO (mole-%) | 13.4 | 17.6 | 23.6 | 13.5 |
| $La_2O_3$ (mole-%) | 11.4 | 15.4 | 15.2 | 17.1 |
| $B_2O_3$ (mole-%) | 37.4 | 49.4 | 37.1 | 32.3 |
| $TiO_2$ (mole-%) | 21.3 | 12.1 | 10.5 | 33.8 |
| $Al_2O_3$ (mole-%) | 16.6 | 5.4 | 13.6 | 3.4 |

TABLE 2-continued

Analyzed Composition (mole-%) and Thermal Properties of Examples of Silicate-Free Titanium Sealing-Glasses Including Lanthanum

| Glass Composition | TIG-9 | TIG-17 | TIG-23 | TIG-24 |
|---|---|---|---|---|
| $T_g$ (°C.) | 659 | 652 | 646 | 662 |
| Coefficient of Thermal Expansion (× 10$^{-7}$ °C.$^{-1}$) | 74 | 81 | 89 | 92 |
| Dissolution Rate (g-cm$^{-2}$min$^{-1}$) | 1.0 × 10$^{-8}$ | 2.5 × 10$^{-9}$ | 4.0 × 10$^{-9}$ | <1.0 × 10$^{-9}$ | thermal properties and a dissolution rate which provides a measure of the aqueous durability. In Table 2 the dissolution rates for each sealing-glass composition are determined from weight-loss measurements on polished glass samples after submersion in deionized water at 70° C. for two weeks. A smaller dissolution rate for a particular sealing-glass composition correlates with an increased resistance of the sealing-glass composition to chemical attack by moisture, water, or body fluids containing water (i.e. an increased aqueous durability).

The hermeticity of the titanium sealing-glass compositions according to the present invention can be measured by forming a glass-to-metal seal comprising at least one body of sealing-glass in contact with titanium or a titanium alloy. Titanium in the form of commercially pure grade 2 titanium (i.e. ≧99% purity), for example, can be used to form a glass-to-metal seal for use in corrosive environments due to its high chemical durability. Pure titanium, however, exhibits an allotropic α-β phase transition at 882° C. that can degrade the original mechanical properties. Thus, a sealing-glass composition according to the present invention should have a sealing temperature, $T_{seal}$, that is less than about 900° C., and preferably less than 882° C. when used for forming a glass-to-metal seal with pure titanium. Alternately, a titanium alloy such as a titanium beta C alloy (also referred to herein as Ti-βC) which is stabilized against the α-β phase transition can be used, thereby allowing a sealing temperature, $T_{seal}$, above 882° C., but preferably less than about 950° C. Such a Ti-βC alloy is further advantageous for providing a room-temperature tensile strength on the order of 900 MPa. The term "titanium" as used herein refers to titanium or any alloy thereof.

FIG. 1 shows a first example of a glass-to-metal seal 100 according to the present invention. In FIG. 1, the glass-to-metal seal 100 is used for forming a hermetically-sealed header for a battery (not shown), with the glass-to-metal seal 100 comprising an electrically-insulating cylindrical sealing-glass body 10 having a composition according to the present invention, with the sealing-glass body 10 contacting on an outer surface thereof a metal header body 20 (e.g. comprising 304 stainless steel, titanium or a titanium alloy) and contacting on an inner surface thereof a cylindrical electrical lead pin 30 (i.e. an electrical feedthrough) formed of titanium (e.g. grade 4 or ≧99.99% purity with a CTE of 93.9×10$^{-7}$° C.$^{-1}$) or Ti-βC (e.g. a titanium alloy comprising titanium alloyed with about 6 weight-% vanadium and about 4 weight-% aluminum, and having a CTE of 95.1×10$^{-7}$° C.$^{-1}$). In the example of FIG. 1, the electrical lead pin 30 can have a diameter of about ⅛ inch; a pair of semi-circular preforms forming the glass body 10 can each have an inner diameter of about ⅛ inch and an outer diameter of about ¼ inch; and the header body 20 can be in the form of a plate having an outer diameter of about 1 inch, an inner diameter of about ¼ inch and a thickness of about 1/16 inch.

In FIG. 1, the glass-to-metal seal 100 can be formed from a pair of semi-circular preforms cast from one of the sealing-glass compositions of the present invention; or alternately a single annular sealing-glass preform can be used. The sealing-glass preforms are fitted between the header body 20 and the electrical lead pin 30 to provide a close-fitting header assembly. A weighted annular graphite fixture can then be provided above the sealing-glass preform(s) to promote a flow of the sealing-glass upon melting to fuse or seal the sealing-glass to the header body 20 and the electrical lead pin 30, thereby forming the glass-to-metal seal 100 upon cooling. For fusing of the sealing-glass to the header body 20 and pin 30, the header assembly can be heated in a continuous-melt or batch furnace to a sealing temperature, $T_{seal}$, of about 775° C. or more (but preferably below the titanium phase transition temperature of 882° C. if a pure titanium pin 30 is used) for a predetermined period of time (e.g. 15 minutes) in an inert ambient (e.g. argon or nitrogen).

The header assembly can then be slowly cooled down to room temperature in a cool-down process that can include an annealing step whereby the glass-to-metal seal 100 is annealed for a predetermined period of time (e.g. about 15 minutes) at a temperature near the glass transition temperature, $T_g$, (e.g. about 640° C.). The exact times and temperatures for forming the glass-to-metal seal 100 and the cool-down and annealing steps can be determined from practice of the present invention to provide a glass-to-metal seal 100 that is hermetic and substantially free defects that can impair the hermeticity or mechanical strength of the seal 100. The completed header 100 can be welded or sealed to a container for forming the battery. Glass-to-metal seals 100 can be similarly formed for other types of electrical components or devices.

Glass-to-metal seals 100 formed from the various titanium sealing-glass compositions including lanthanum in Table 2 can be evaluated for hermeticity by helium leak detection, with the titanium sealing-glass compositions in Table 2 being hermetic to $<10^{-9}$ cm$^3$-sec$^{-1}$ of helium. The integrity of the glass-to-metal seals 100 can also be evaluated by visual observations with low power optical microscopy to or by scanning electron microscopy after cross-sectioning the seals. Such evaluation is useful for detecting any major defects such as bubbles, cracks, or crystallinity within the sealing-glass composition; and for examining interfaces between the sealing-glass composition and the metal body 20 and/or the electrical lead pin 30. The glass-to-metal seals 100 formed according to the present invention provide interfaces with good wetting and adherence characteristics, and the absence of any major defects. The titanium sealing-glass compositions in Table 2 also provide strong glass-to-metal seals 100 to flat titanium coupons (i.e. butt seals).

The aqueous durability of the titanium sealing-glass compositions including lanthanum of the present invention can be compared with silicate- and lanthanum-free titanium sealing glasses by comparing the dissolution rates for each sealing-glass composition. Table 3 lists the compositions and measured thermal properties and dissolution rates for several silicate- and lanthanum-free sealing glasses which provide hermetic glass-to-metal seals with titanium and titanium alloys. However, the aqueous durabilities of the silicate- and lanthanum-free sealing glasses of Table 3 are much poorer than the aqueous durabilities for the titanium sealing glasses containing lanthanum according to the present invention. For example, the TIG-9 sealing-glass composition of the present invention in Table 2 is a hundred times more resistant to dissolution upon exposure to water than the best of the silicate- and lanthanum-free sealing glasses in Table 3; whereas the TIG-24 sealing-glass composition of the present invention in Table 2 has an aqueous durability that is a thousand-fold better (i.e. a thousand-fold smaller dissolution rate) than that of any of the silicate- and lanthanum-free sealing glasses of Table 3. The excellent aqueous durabilities of the titanium sealing-glass compositions of the present invention in Table

TABLE 3

Composition (mole-%) and Thermal Properties of Examples of Silicate- and Lanthanum-Free Sealing-Glasses

| Glass Composition | SrBAl-1 | BaBAl-2 | CaBAl-17 |
| --- | --- | --- | --- |
| CaO (mole-%) | 0 | 0 | 50 |
| SrO (mole-%) | 45 | 0 | 0 |
| BaO (mole-%) | 0 | 40 | 0 |
| Al$_2$O$_3$ (mole-%) | 15 | 20 | 20 |
| B$_2$O$_3$ (mole-%) | 40 | 40 | 30 |
| Tg (°C.) | 575 | 542 | 592 |
| Coefficient of thermal Expansion ($\times 10^{-7}$ °C.$^{-1}$) | 98 | 104 | 91 |
| Dissolution Rate (g-cm$^{-2}$min$^{-1}$) | $2.0 \times 10^{-4}$ | $1.0 \times 10^{-5}$ | $1.0 \times 10^{-6}$ |

2 permits their use for in vivo component or device applications; whereas the silicate- and lanthanum-free sealing-glass compositions of Table 3 would not normally be used in vivo due to their poorer aqueous durabilities.

Figure 2:
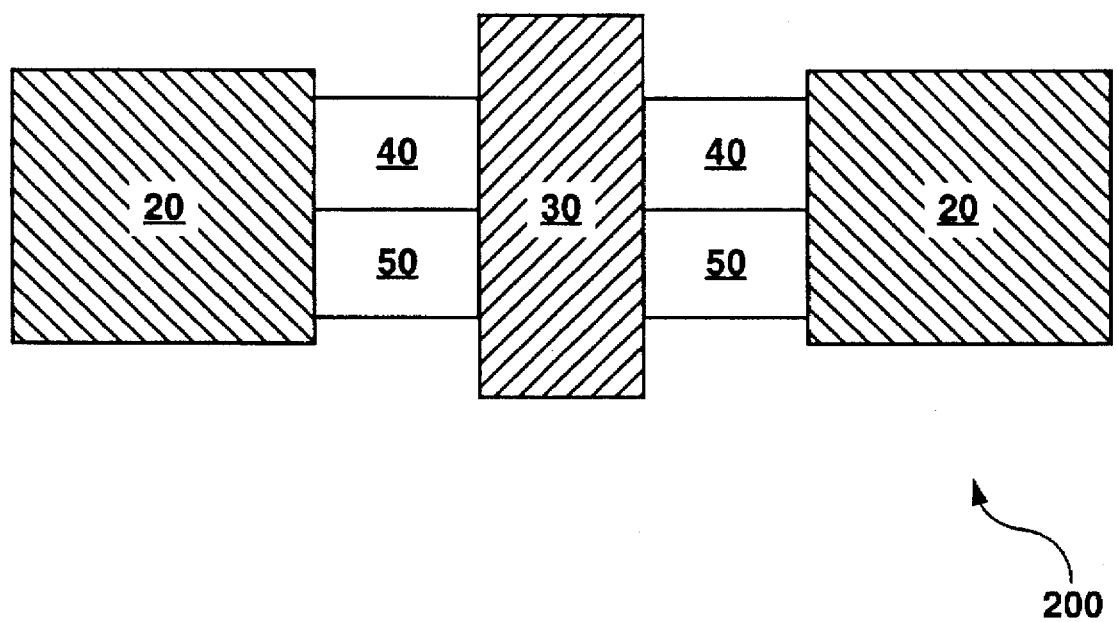
FIG. 2 shows a schematic cross-section diagram of a second example of a compound glass-to-metal seal formed with a titanium sealing-glass composition according to the present invention.

FIG. 2 shows a second example of a glass-to-metal seal according to the present invention. In FIG. 2, the glass-to-metal seal is used for forming a hermetic seal between a titanium header body 20 and a titanium electrical lead pin 30 (i.e. an electrical feedthrough) in a header for a lithium battery (not shown). The glass-to-metal seal in the second example of FIG. 2 is a compound seal 200 comprising an outer seal 40 formed of a titanium sealing-glass composition including lanthanum (i.e. a sealing-glass composition of the present invention selected according to Table 1 or Table 2) for providing a high aqueous durability (i.e. a substantial chemical resistance to attack by moisture, water or body fluids); and an inner seal 50 comprising a sealing-glass composition having a substantial chemical resistance to attack by lithium (e.g. a silicate- and lanthanum-free sealing-glass composition selected from Table 3). Each of the seals 40 and 50 in FIG. 2 is formed from a sealing-glass composition having a coefficient of thermal expansion close to that of titanium or a titanium alloy. The compound glass-to-metal seal 200 in FIG. 2 is expected to be particularly useful for biomedical applications (i.e. in vivo use), since no single sealing-glass composition is presently known which provides an adequate chemical resistance to both body fluids (or water) and to lithium, and which has a coefficient of thermal expansion that permits sealing to titanium or titanium alloys.

The compound glass-to-metal seal 200 in FIG. 2 can be formed similarly to the example of FIG. 1 by providing sealing-glass preforms for the outer seal 40 and the inner seal 50. The sealing-glass preforms, header body 20 and electrical lead pin 30 can be assembled with a weighted annular graphite fixture provided above the preforms to promote a flow of the sealing glasses upon melting. The header assembly can then be heated to a predetermined sealing temperature, $T_{seal}$, of about 775° C. or more (but preferably below the titanium phase transition temperature of 882° C. when using pure titanium for the body 20 and/or the pin 30) for about 15 minutes in an inert ambient to melt the sealing-glass preforms and to fuse the preforms together, and to the body 20 and pin 30, thereby forming the compound glass-to-metal seal 200 upon cooling. The header assembly can then be slowly cooled down to room temperature with an annealing step preferably being provided at a temperature near the glass transition temperature, $T_g$, of each of the sealing glasses (e.g. a first annealing step near 640° C. for about 15 minutes for a TIG-23 sealing-glass composition forming the outer seal 40; and a second annealing step near 540° C. for a BaBAl-2 sealing-glass composition forming the inner seal 50).

The matter set forth in the foregoing description and accompanying drawings is offered by way of illustration only and not as a limitation. Other applications and variations of the titanium sealing glasses and seals formed therefrom will become evident to those skilled in the art. In particular, the titanium sealing-glass compositions of the present invention have applications for forming glass-to-metal seals for electrical feedthroughs for many types of devices including implantable devices such as batteries, heart pacemakers, defibrillators, pumps or the like. The actual scope of the invention is intended to be defined in the following claims when viewed in their proper perspective based on the prior art.

What is claimed is:

1. A glass-to-metal seal having an improved aqueous durability, comprising:
    a metal consisting of titanium or a titanium alloy; and
    a sealing-glass in contact with the metal and comprising:
        10–43 mole-% CaO,
        8–30 mole-% $La_2O_3$, and
        31–57 mole-% $B_2O_3$.

2. The glass-to-metal seal of claim 1 further having a sealing temperature of less than about 900° C.

3. The glass-to-metal seal of claim 1 further having a coefficient of thermal expansion in the range of about $70-100 \times 10^{-7}$ °C.$^{-1}$.

4. The glass-to-metal seal of claim 1 further being substantially resistant to chemical attack upon exposure to water.

5. The glass-to-metal seal of claim 1 wherein the sealing-glass further includes at least one oxide selected from the group consisting of $TiO_2$ in the amount of 0–41 mole-% and $Al_2O_3$ in the amount of 0–28 mole-%.

6. The glass-to-metal seal of claim 5 wherein all percentages total 100.

7. The glass-to-metal seal of claim 6 wherein:
    CaO is present in the amount of about 10–25 mole-%;
    $La_2O_3$ is present in the amount of about 10–20 mole-%;
    $B_2O_3$ is present in the amount of about 30–50 mole-%;
    $TiO_2$ is present in the amount of about 10–35 mole-%; and
    $Al_2O_3$ is present in the amount of about 0–20 mole-%.

8. The glass-to-metal seal of claim 7 wherein:
    CaO is present in the amount of about 13 mole-%;
    $La_2O_3$ is present in the amount of about 11 mole-%;
    $B_2O_3$ is present in the amount of about 37 mole-%;
    $TiO_2$ is present in the amount of about 21 mole-%; and
    $Al_2O_3$ is present in the amount of about 17 mole-%.

9. The glass-to-metal seal of claim 7 wherein:
    CaO is present in the amount of about 18 mole-%;
    $La_2O_3$ is present in the amount of about 15 mole-%;
    $B_2O_3$ is present in the amount of about 49 mole-%;
    $TiO_2$ is present in the amount of about 12 mole-%; and
    $Al_2O_3$ is present in the amount of about 5 mole-%.

10. The glass-to-metal seal of claim 7 wherein:
    CaO is present in the amount of about 24 mole-%;
    $La_2O_3$ is present in the amount of about 15 mole-%;
    $B_2O_3$ is present in the amount of about 37 mole-%;
    $TiO_2$ is present in the amount of about 11 mole-%; and
    $Al_2O_3$ is present in the amount of about 14 mole-%.

11. The glass-to-metal seal of claim 7 wherein:
    CaO is present in the amount of about 14 mole-%;
    $La_2O_3$ is present in the amount of about 17 mole-%;
    $B_2O_3$ is present in the amount of about 32 mole-%;
    $TiO_2$ is present in the amount of about 34 mole-%; and
    $Al_2O_3$ is present in the amount of about 3 mole-%.

12. An electrical feedthrough for use in an implantable device, comprising:
    a sealing-glass composition including
        10–43 mole-% CaO,
        8–30 mole-% $La_2O_3$, and
        31–57 mole-% $B_2O_3$,
    in contact with titanium or a titanium alloy.

13. The electrical feedthrough of claim 12 further including at least one oxide selected from the group consisting of $TiO_2$ in the amount of 0–41 mole-% and $Al_2O_3$ in the amount of 0–28 mole-%.

14. The electrical feedthrough of claim 12 wherein the implantable device is selected from the group consisting of batteries, heart pacemakers, defibrillators, and pumps.

15. The electrical feedthrough of claim 14 wherein the implantable device is a lithium battery, and wherein the electrical feedthrough further comprises an inner seal having a sealing-glass composition that has a substantial chemical resistance to lithium.

16. The electrical feedthrough of claim 15 wherein the inner seal comprises a silicate-free and lanthanum-free sealing-glass composition.

17. A glass-to-metal seal for use in a lithium battery, comprising:
    an outer glass-to-metal seal comprising a first sealing-glass composition in contact with titanium or a titanium alloy for providing a substantial chemical resistance to water; and
    an inner glass to metal seal superposed with the outer glass-to-metal seal comprising a sealing-glass composition having a substantial chemical resistance to lithium;
    wherein the first-sealing glass composition includes:
        CaO in the amount of 10–43 mole-%;
        $La_2O_3$ in the amount of 8–30 mole-%;
        $B_2O_3$ in the amount of 31–57 mole-%;
        $TiO_2$ in the amount of 0–41 mole-%; and
        $Al_2O_3$ in the amount of 0–28 mole-%.

* * * * *